United States Patent
Ide et al.

(10) Patent No.: US 11,230,515 B2
(45) Date of Patent: Jan. 25, 2022

(54) METHODS FOR REMOVING IMPURITIES FROM A HYDROCARBON STREAM AND THEIR USE IN AROMATIC ALKYLATION PROCESSES

(71) Applicant: ExxonMobil Chemical Patents Inc., Baytown, TX (US)

(72) Inventors: Matthew S. Ide, Doylestown, PA (US); Doron Levin, Highland Park, NJ (US); Scott J. Weigel, Allentown, PA (US); Brett T. Loveless, Houston, TX (US); Jean W. Beeckman, Columbia, MD (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 17 days.

(21) Appl. No.: 16/497,256

(22) PCT Filed: Mar. 19, 2018

(86) PCT No.: PCT/US2018/023091
§ 371 (c)(1),
(2) Date: Sep. 24, 2019

(87) PCT Pub. No.: WO2018/183012
PCT Pub. Date: Oct. 4, 2018

(65) Prior Publication Data
US 2020/0377431 A1    Dec. 3, 2020

Related U.S. Application Data

(60) Provisional application No. 62/478,340, filed on Mar. 29, 2017, provisional application No. 62/478,237, filed on Mar. 29, 2017.

(30) Foreign Application Priority Data

Jun. 2, 2017    (EP) .................................... 17174274

(51) Int. Cl.
*C07C 7/13*    (2006.01)
*B01J 29/70*    (2006.01)
(Continued)

(52) U.S. Cl.
CPC ................. *C07C 7/13* (2013.01); *B01J 21/12* (2013.01); *B01J 29/7007* (2013.01);
(Continued)

(58) Field of Classification Search
None
See application file for complete search history.

(56) References Cited

U.S. PATENT DOCUMENTS

| 4,891,458 A | 1/1990 | Innes et al. |
| 4,992,606 A | 2/1991 | Kushnerick et al. |

(Continued)

FOREIGN PATENT DOCUMENTS

| CN | 102921373 | 2/2013 |
| WO | 98/07673 A | 2/1998 |

(Continued)

OTHER PUBLICATIONS

Rouquerol, J. et al. "International union of pure and applied chemistry physical chemistry division, commission on colloid and surface chemistry, Subcommittee on characterization of porous solids—recommendations for the characterization of porous solids", Pure and Appl. Chem., vol. 66, No. 8, pp. 1739-1758, Jan. 1, 1994.
(Continued)

*Primary Examiner* — Philip Y Louie
*Assistant Examiner* — Alyssa L Cepluch

(57) ABSTRACT

Methods for removing impurities from a hydrocarbon stream using a guard bed material are disclosed. The guard bed material includes compositions which comprises a zeolite and a mesoporous support or binder. The zeolite has a Constraint Index of less than 3. The mesoporous support or
(Continued)

binder comprises a mesoporous metal oxide having a particle diameter of greater than or equal to 20 μm at 50% of the cumulative pore size distribution ($d_{50}$), a pore volume of less than 1 cc/g, and an alumina content of greater than 75%, by weight. Also disclosed are processes for producing monoalkylated aromatic compounds (e.g., ethylbenzene or cumene) using impure feed streams that are treated by the disclosed methods to remove impurities which act as catalyst poisons to downstream alkylation and/or transalkylation catalysts.

15 Claims, 2 Drawing Sheets

(51) Int. Cl.
*B01J 35/02* (2006.01)
*B01J 35/10* (2006.01)
*C07C 2/66* (2006.01)
*C07C 6/12* (2006.01)
*B01J 21/12* (2006.01)

(52) U.S. Cl.
CPC ......... *B01J 29/7038* (2013.01); *B01J 35/023* (2013.01); *B01J 35/1019* (2013.01); *B01J 35/1042* (2013.01); *C07C 2/66* (2013.01); *C07C 6/126* (2013.01); *B01J 29/70* (2013.01); *C07C 2529/70* (2013.01)

(56) References Cited

U.S. PATENT DOCUMENTS

| | | | |
|---|---|---|---|
| 5,049,536 A * | 9/1991 | Bellussi | C07C 2/10 502/235 |
| 5,334,795 A | 8/1994 | Chu et al. | |
| 5,545,788 A | 8/1996 | Cheng et al. | |
| 5,600,048 A | 2/1997 | Cheng et al. | |
| 5,942,650 A | 8/1999 | Gajda | |
| 7,425,659 B2 | 9/2008 | Clark | |
| 7,645,913 B2 | 1/2010 | Clark et al. | |
| 8,022,261 B2 | 9/2011 | Kalyanaraman et al. | |
| 8,247,629 B2 | 8/2012 | Clark et al. | |
| 8,840,779 B2 | 9/2014 | McCarthy et al. | |
| 9,382,170 B1 | 7/2016 | Vincent et al. | |
| 10,118,165 B2 | 11/2018 | Lai et al. | |
| 2002/0042548 A1 | 4/2002 | Dandekar et al. | |
| 2004/0138051 A1 | 7/2004 | Shan et al. | |
| 2007/0042905 A1 | 2/2007 | Negiz et al. | |
| 2008/0319242 A1 | 12/2008 | Clark et al. | |
| 2009/0306446 A1* | 12/2009 | Clark | B01J 29/06 585/449 |
| 2011/0079145 A1 | 4/2011 | Dolan et al. | |
| 2011/0111232 A1* | 5/2011 | Chaumonnot | C01B 39/00 428/404 |
| 2012/0083635 A1 | 4/2012 | Boldingh et al. | |
| 2012/0088937 A1 | 4/2012 | Jan et al. | |
| 2013/0137910 A1 | 5/2013 | Vincent et al. | |
| 2015/0038753 A1 | 2/2015 | Mertens et al. | |
| 2015/0197466 A1 | 7/2015 | Maerz et al. | |

FOREIGN PATENT DOCUMENTS

| | | |
|---|---|---|
| WO | 2014/182294 A | 11/2014 |
| WO | 2016/099715 | 6/2016 |
| WO | 2018/183009 A | 10/2018 |

OTHER PUBLICATIONS

UOP: "UOP Versal Alumina: A family of High Performance Powders", Apr. 1, 2012. URL:http://www.uop.com/?document=uop-versal-alumina-brochure&download=1.

Sasol: "Sasol Germany GmbH", Jan. 1, 2003, URL:http://www.sasoltechdata.com/tds/PURALCATAPAL.pdf.

* cited by examiner

METHODS FOR REMOVING IMPURITIES FROM A HYDROCARBON STREAM AND THEIR USE IN AROMATIC ALKYLATION PROCESSES

CROSS REFERENCE TO RELATED APPLICATIONS

This application is a National Phase Application of PCT Application Serial No. PCT/US2018/023091, filed Mar. 19, 2018, which claims the benefits of and priorities to U.S. Provisional Application No. 62/478,340, entitled "METHODS FOR REMOVING IMPURITIES FROM A HYDROCARBON STREAM AND THEIR USE IN AROMATIC ALKYLATION PROCESSES", filed on Mar. 29, 2017, EP application 17174274.5, filed on Jun. 2, 2017, and U.S. Provisional Application No. 62/478,237, entitled "CATALYST COMPOSITIONS AND THEIR USE IN AROMATIC ALKYLATION PROCESSES", filed on Mar. 29, 2017, the disclosures of which are all incorporated by reference in their entireties.

FIELD OF THE INVENTION

This invention relates to a method for removing impurities from a hydrocarbon stream using a guard bed material. The guard bed material comprises a composition having an increased capacity to adsorb catalyst poisons from hydrocarbon streams. This invention also relates to the use of the guard bed materials to remove such catalyst poisons from untreated (i.e., impure) feed streams having one or more impurities which cause deactivation of the downstream catalysts employed in hydrocarbon conversion processes, such as those that produce mono-alkylated aromatic compounds.

BACKGROUND OF THE INVENTION

In a typical aromatic alkylation process, an aromatic compound is reacted with an alkylating agent, such as an olefin, in the presence of acid catalyst. For example, benzene can be reacted with ethylene or propylene to produce ethylbenzene or cumene, both of which are important intermediates in the chemical industry. In the past, commercial aromatic alkylation processes normally used $AlCl_3$ or $BF_3$ as the acid catalyst, but more recently these materials have been replaced by molecular sieve-based catalysts.

Aromatics alkylation processes employing molecular sieve-based catalysts may be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve-based catalysts tend to be more sensitive to the presence of catalyst poisons in the feed streams, especially those with a compound having at least one of the following elements: nitrogen, halogens, oxygen, sulfur, arsenic, selenium, tellurium, phosphorus, and Group 1 through Group 12 metals. Such impurities reduce the acid activity of such molecular sieve-based catalyst and hence decrease the cycle time between required regenerations of such catalyst.

The use of guard beds to remove trace contaminants from hydrocarbon feed streams is well known in the art. This is especially true for petrochemical and specialty chemical operations where product purity is critical. Normally, guard bed materials that contain bentonite clay, kaolin clay, special activated aluminas or molecular sieves are used and are placed upstream of a reaction vessel containing an acidic molecular sieve-based catalyst. These guard bed materials trap impurities in the feed streams so that product purity specifications can be met and poisoning of such catalyst can be reduced. However, such guard bed materials have limited capacity to adsorb impurities from aromatic feed streams to the low levels required for use in liquid phase alkylation processes which employ acidic molecular sieve-based catalysts. Therefore, a need exists for a guard bed material with an increased capacity to adsorb impurities more effectively. It is desirable to remove such impurities from the feed streams to such aromatic alkylation processes and thereby reduce the deactivation of the downstream acidic molecular sieve-based catalyst used in alkylation and/or transalkylation reactions.

SUMMARY OF THE INVENTION

It has now been found that the guard bed materials which comprise the compositions of this invention have higher acidity and improved accessability to their acid sites. Such compositions exhibit an improved capacity to remove catalyst poisons from hydrocarbon streams, particularly feed streams which comprise benzene and ethylene or propylene, to processess to produce mono-alkylated aromatic compounds, such as ethylbenzene and cumene. When catalyst poisons are removed, the downstream zeolite-based alkylation and transalkylation catalysts exhibit decreased deactivation and increased cycle length.

In a first aspect, this invention is a method for removing impurities from a hydrocarbon stream. In step (a) of the method, an untreated (i.e., impure) feed stream and a guard bed material are supplied. The guard bed material comprises any one of the compositions of this invention, described herein. The feed stream comprises one or more hydrocarbons and undesirable impurities. In one or more embodiments, the impurities comprise at least one compound having at least one of the following elements: nitrogen, halogens, oxygen, sulfur, arsenic, selenium, tellurium, phosphorus, and Group 1 through Group 12 metals. In step (b) of the method, at least a portion of the untreated feed stream is contacted with the guard bed material under treatment conditions to remove at least a portion of the impurities and produce a treated feed stream having a reduced amount of impurities. In one or more embodiments, the guard bed material and the untreated feed stream are supplied to a guard bed zone for contacting therein.

In a second aspect, this invention is a process for producing a mono-alkylated aromatic compound. In an alkylation step (a) of the process, at least a portion of a treated feed stream and an alkylating agent stream is contacted with an alkylation catalyst under suitable at least partially liquid phase alkylation conditions. The treated feed stream comprises an alkylatable aromatic compound which is made by the method for removing impurities from a hydrocarbon stream of the second aspect of this invention, described herein. At least a portion of the alkylatable aromatic compound in the treated feed stream is alkylated with said alkylating agent stream to produce an effluent stream. The effluent stream comprises the mono-alkylated aromatic compound and poly-alkylated aromatic compounds.

Advantageously, the treated feed stream and the guard bed material as well as an alkylating agent are supplied to a guard bed zone. In the reaction zone, the alkylating agent stream is contacted with the guard bed material and the treated feed stream to produce additional mono-alkylated and poly-alkylated aromatic compounds at the same time as the impurities are removed from the untreated feed stream. In separation step (b), the effluent stream is separated to recover a mono-alkylated aromatic compound stream and a poly-alkylated aromatic compounds stream.

Advantageously, the alkylation catalyst comprises an acidic aluminosilicate. The aluminosilicate is any one of a MCM-22 family molecular sieve, faujasite, mordenite, zeolite beta, or combinations of two or more thereof.

Advantageously, the poly-alkylated aromatic compounds stream is then contacted with another portion of the treated feed stream with a transalkylation catalyst under suitable at least partially liquid phase transalkylation conditions to transalkylate said poly-alkylated aromatic compound stream with said alkylatable aromatic compound and produce additional said mono-alkylated aromatic compound. The transalkylation catalyst is a large pore molecular sieve or a MCM-22 family material.

In one or more embodiments, the alkylatable aromatic compound is benzene. In such embodiments, when the alkylating agent is propylene, the mono-alkylated aromatic compound is ethylbenzene and the poly-alkylated aromatic compound is poly-ethylbenzene. Similarly, when the alkylating agent is propylene, the mono-alkylated aromatic compound is cumene and the poly-alkylated aromatic compound is poly-isopropylbenzene.

In a third aspect, this invention is a guard bed material which comprises a zeolite and a mesoporous support or mesoporous binder. The mesoporous support or mesoporous binder comprises a mesoporous metal oxide. The zeolite has a Constraint Index of less than 3. The mesoporous metal oxide has a particle diameter of greater than or equal to 20 µm at 50% of the cumulative particle size distribution ($d_{50}$). The pore volume of the mesoporous metal oxide is less than 1 cc/g in one or more embodiments.

Advantageously, the zeolite which has a Constraint Index of less than 3 includes, but is not limited to, any one of zeolite beta, faujasite, mordenite, a MCM-22 family material, as defined herein, and mixtures of two or more thereof.

Advantageously, the mesoporous metal oxide includes, but is not limited to, any one of aluminum hydroxide, boehmite, pseudoboehmite alumina, aluminum oxide, amorphous silica-alumina and mixtures of two or more thereof.

Advantageously, the guard bed material has an Alpha Value of greater than or equal to 500, and/or a Collidine Uptake of greater than or equal to 600 µmoles/g, and/or a temperature programmed ammonia desportion of greater than or equal to 0.70 meq/g.

DETAILED DESCRIPTION OF THE INVENTION

Figure 1:
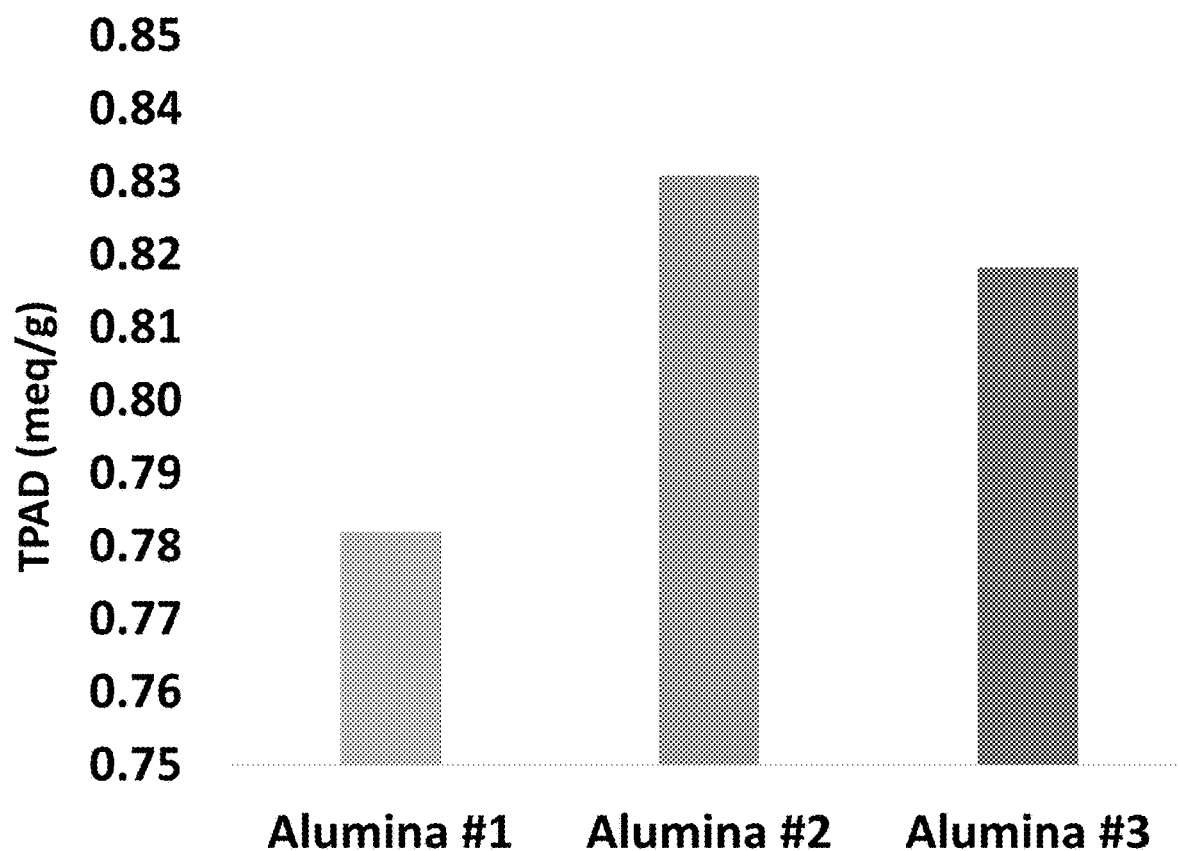
FIG. 1 shows the performance of the guard bed materials of Example 6 as measured by the temperature programmed ammonia desorption for the pseudoboehmite aluminas, VERSAL-300™ (Alumina #1) and PURAL NG™ (Alumina #2) and the amorphous, preciptated silica-alumina, SIRAL-20™ (Alumina #3).

Increased capacity to adsorb catalyst poisons from hydrocarbons streams is exhibited by the guard bed materials which comprises any one of the compositions of this invention, when used in a process for producing a mono-alkylated aromatic compound, preferably ethylbenzene or cumene, by the alkylation of alkylatable aromatic compound, preferably benzene, with an with an alkylating agent, preferably ethylene or propylene, in the presence of such composition under at least partial liquid phase conditions.

Definitions

The term "guard bed material," as used herein, includes a material that can act to increase the rate constant in a chemical reaction, as well as a material that can act to adsorb catalyst poisons from a hydrocarbon stream.

The term "alkylatable aromatic compound," as used herein, means an aromatic compound that may receive an alkyl group. One non-limiting example of an alkylatable aromatic compound is benzene.

The term "alkylating agent", as used herein, means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "aromatic," as used herein, in reference to the alkylatable aromatic compounds which are useful herein, is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "at least partially liquid phase," as used herein, means a mixture having at least 1 wt. % liquid phase, optionally at least 5 wt. % liquid phase, at a given temperature, pressure, and composition.

The term "catalyst poisons," as used herein, means one or more impurities, defined herein, which acts to reduce the cycle-length of a molecular sieve or zeolite.

The term "Constraint Index" as used herein is defined in U.S. Pat. Nos. 3,972,832 and 4,016,218.

The term "normalized", as used herein with respect to a series of numerical values, means to scale each value by a common factor for purposes of comparison. The normalized value for the common factor will equal 1.

The term "framework type", as used herein, has the meaning described in the "Atlas of Zeolite Framework Types," by Ch. Baerlocher, W. M. Meier and D. H. Olson (Elsevier, 5th Ed., 2001).

The terms "cumulative particle size distribution ($d_{50}$)," and "cumulative particle size distribution," as used herein, mean the median value of the particle size distribution in a sample where the value of the particle diameter is at 50% of the cumulative distribution. For example, if $d_{50}$=20 µm for a sample, then 50% of the particles in the sample are larger than 20 µm, and 50% smaller than 20 µm.

The term "pore volume", as used herein, means the volume of the pores in a material as measured by mercury intrusion as measure by ASTM method D4284, and it is expressed as cc/g.

The term "Alpha Value", as used herein, is a measure of the cracking activity and is determined in accordance with the method described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

The term "Collidine Uptake", as used herein, is a measure of the acidity of a material, and Collidine Uptake is determined by the method described in the Examples and expressed as the millimoles of collidine (a type of catalyst poison) absorbed per gram of material.

The term "Temperature Programmed Ammonia Desportion" or "TPAD", as used herein, is also a measure of the acidity of a material, and TPAD is determined by the method described in the Examples and expressed as milliequivalents of H+ sites per gram of sample (meq/g).

Zeolite beta has a *BEA framework type and is described in U.S. Pat. No. 3,308,069 and U.S. Reissue Pat. No. 28,341.

Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. EMM-34, also referred to as meso-mordenite, is a zeolite synthesized from structure directing agents TEA (tetraethyl ammonium cation) or MTEA (methyl triethyl ammonium cation) and having a mesopore surface area of greater than 30 $m^2/g$ and comprising agglomerates composed of primary crystallites, wherein the primary crystallites have an average primary crystal size as measured by TEM of less than 80 nm and an aspect ratio of less than 2, as disclosed in International Publication WO2016/126431, incorporated by reference where permitted. UZM-14 is described in U.S. Publication 20090325785 A1. The MOR framework type includes various natural and synthetic forms of mordenite, including TEA-mordenite, EMM-34 and UZM-14.

The term "MCM-22 family material" (or "MCM-22 family molecular sieve"), as used herein, can include:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);

(ii) molecular sieves made from a common second degree building block, a 2-dimensional tiling of such MWW framework type unit cells, forming a "monolayer of one unit cell thickness," preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697; and an EMM-10 family molecular sieve (described or characterized in U.S. Pat. Nos. 7,959,899 and 8,110,176; and U.S. Patent Application Publication No. 2008/0045768), such as EMM-10, EMM-10-P, EMM-12 and EMM-13. Typically, the molecular sieve of the MCM-22 family is in the hydrogen form and having hydrogen ions, for example, acidic.

Related zeolites to be included in the MCM-22 family are UZM-8 (described in U.S. Pat. No. 6,756,030), UZM-8HS (described in U.S. Pat. No. 7,713,513), UZM-37 (described in U.S. Pat. No. 8,158,105), and MIT-1 is described in Chem. Sci., 2015, 6, 6320-6324, all of which are also suitable for use as the molecular sieve of the MCM-22 family.

The term "hydrocarbon", as used herein, means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n, where n is the number of carbon atom(s) per molecule.

The term "mono-alkylated aromatic compound", as used herein, means an aromatic compound that has only one alkyl substituent. Non-limiting examples of mono-alkylated aromatic compounds are ethylbenzene, iso-propylbenzene (cumene), and sec-butylbenzene.

The term "poly-alkylated aromatic compound", as used herein, means an aromatic compound that has more than one alkyl substituent. A non-limiting example of a poly-alkylated aromatic compound is poly-ethylbenzene, e.g., di-ethylbenzene, tri-ethylbenzene, and poly-isopropylbenzene, e.g., di-isopropylbenzene, and tri-isopropylbenzene.

The term "impurities", as used herein, includes, but is not limited to, compounds having at least one of the following elements: nitrogen, halogen, oxygen, sulfur, arsenic, selenium, tellurium, phosphorus, and Group 1 through Group 12 metals.

The term "large pore molecular sieve", as used herein, means molecular sieve preferably having a Constraint Index of less than 2.

Suitable large pore molecular sieves include the aforementioned zeolite beta and mordenite as well as faujasite including zeolite Y, Ultrastable Y (USY), Dealuminized Y (Deal-Y), Ultrahydrophobic Y (UHP-Y), Rare earth exchanged Y (REY). Also included is ZSM-2, ZSM-3, ZSM-4, ZSM-12, ZSM-14, ZSM-18, ZSM-20, ZSM-50, MCM-68 ECR-4, ECR-17, ECR-32, ECR-35 and mixtures of two or more thereof.

Zeolite Y is described in U.S. Pat. No. 3,130,007. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Ultrahydrophobic Y (UHP-Y) is described in U.S. Pat. No. 4,401,556. Rare earth exchanged Y (REY) is described in U.S. Pat. No. 3,524,820.

Zeolite ZSM-2 is described in U.S. Pat. No. 3,411,874. Zeolite ZSM-3 is described in U.S. Pat. No. 3,415,736. ZSM-4 is described in U.S. Pat. No. 4,021,447. ZSM-12 is described in U.S. Pat. No. 3,832,449. ZSM-14 is described in U.S. Pat. No. 3,923,636. ZSM-18 is described in U.S. Pat. No. 3,950,496. Zeolite ZSM-20 is described in U.S. Pat. No. 3,972,983. ZSM-50 is described in U.S. Pat. No. 4,640,829. MCM-68 is described in U.S. Pat. No. 6,049,018. ECR-4 is described in U.S. Pat. No. 4,965,059. ECR-17 is described in EP Publication EP0259526. ECR-32 is described in U.S. Pat. No. 4,931,267. ECR-35 is described in U.S. Pat. No. 5,116,590.

The term "surface area", as used herein, means the surface area of a material or catalyst composition as determined by mercury intrusion tests performed in accordance with ASTM method D4284.

The term mesoporous, as used herein, means a material containing pores with diameters between 2 and 50 nm.

The term "comprising" (and its grammatical variations), as used herein, is used in the inclusive sense of "having" or "including" and not in the exclusive sense of "consisting only of" The terms "a" and "the", as used herein are understood to encompass the plural as well as the singular.

The entire contents of each and every aforementioned patents and publications are incorporated herein by reference in their entireties.

Guard Bed Material and Composition

Guard bed materials which comprise one or more compositions are one aspect of this invention. Such compositions comprise a zeolite and a mesoporous support or mesoporous binder. The mesoporous support or mesoporous binder comprises a mesoporous metal oxide having a particle diameter of greater than or equal to 20 µm at 50% of the cumulative particle size distribution ($d_{50}$). The pore volume of the mesoporous metal oxide is less than 1 cc/g in one or more embodiments.

The zeolite has a Constraint Index of less than 3, preferably less than 2, most preferably less than 1. The zeolite which has a Constraint Index of less than 3 includes, but is not limited to, a zeolite having the framework structure of BEA*, FAU, MOR, MWW and mixtures of two or more thereof. The BEA* framework structure zeolite comprises zeolite beta. The FAU framework structure comprises faujasite, zeolite Y, USY, Deal-Y, UHP-Y, and REY. The MOR framework structure comprises mordenite, TEA-mordenite, EMM-34 (meso-mordenite). The MWW framework structure comprises any one of the MCM-22 family materials, defined herein. Other zeolites having a Constraint Index of less than 3 include, but are not limited to, ZSM-4, ZSM-12, ZSM-20, ZSM-50 and MCM-68. Mixtures of these zeolites which have a Constraint Index of less than 3 are contemplated. The preferred zeolite is zeolite beta.

The $Si/Al_2$ molar ratio of the zeolite of the composition is less than or equal to 50, or in the range of from 10 to 50.

The mesoporous metal oxide has a particle diameter of greater than or equal to 20 µm at 50% of the cumulative particle size distribution ($d_{50}$). Such $d_{50}$ particle diameter may be greater than or equal to 25 µm, or greater than or equal to 35 µm, or grater than or equal to 50 µm at 50% of the cumulative particle size distribution ($d_{50}$). The $d_{50}$ particle diameter may be in the range from 20 µm up to 60 µm, or in the preferred range of from 25 µm to 50 µm.

In some embodiments, the pore volume of the mesoporous less than or equal to 0.75, or less than or equal to 0.5, or in the preferred range of 0.45 to 0.75 cc/g.

The mesoporous metal oxide includes, but is not limited to, any one of aluminum hydroxide, boehmite, pseudoboehmite alumina, aluminum oxide, amorphous silica-alumina and mixtures of two or more thereof. The preferred mesoporous oxide is pseudoboehmite alumina or an amorphous, precipitated silica-alumina.

The alumina content of said mesoporous metal oxide is greater than or equal to 75% or in the range of from 75% to 95%, by weight.

The ratio of the zeolite to the mesoporous metal oxide is in the range of from 1:99 to 100:0, or in the range from 95:5 to 5:95, or in the range from 90:10 to 10:90, or in the range from 80:20 to 10:90, or in the range from 65:35 to 35:65, by weight.

The catalytic activity of the guard bed material and/or compositions of this invention can be measured by its n-hexane cracking ability as measured by the Alpha Value, as defined herein. The Alpha Value is greater than or equal to 500, or greater than or equal to 550, or greater than or equal to 600, or greater than equal to 650, or greater than equal to 700, or greater than or equal to 750. The Alpha Value may be in the range of greater than 500 up to 800, or in the preferred range of 600 up to 760.

The poison capacity of the guard bed material and/or compositions of this invention may be measured by its acidity. One measure of acidity is the Collidine Uptake, as defined herein. The Collidine Uptake is greater than or equal to 600 µmoles/g, or greater than equal to 650 µmoles/g, or in the preferred range of 600 to 675 µmoles/g.

Another measure of acidity of the guard bed material and/or compositions of this invention is the Temperature Programmed Ammonia Desportion or TPAD. The TPAD is greater than or equal to 0.70 meq/g, or greater than or equal to 0.75 meq/g, or greater than or equal to 0.80 meq/g, or in the preferred range of 0.70 meq/g to 0.85 meq/g.

Not to be bound by any theory, it is believed that the lower surface area and larger particle size of the mesoporous metal oxides used in the guard bed material and/or compositions of this invention may create a more open pore network thereby providing greater acccessablity to the strong acid sites on the exterior and the interior of the zeolite of the material or composition, as compared to smaller particle, higher surface area mesoporous metal oxides.

The method of making the composition is not particularly limited. It may be made by any suitable method known in the art for combining a zeolite and a mesoporous metal oxide, such as for example via co-extrusion. That is, the zeolite and the mesoporous metal oxide may be co-extruded to form one or more of the compositions of this invention.

Method for Removing Impurities from Hydrocarbon Streams

Another aspect of this invention is a method for removing impurities from a hydrocarbon stream, such as for example, a feed stream comprising an alkylatable aromatic compound and optionally an alkylating agent. Such hydrocarbon stream often contain undesireable impurities, as defined herein and are an impure stream. In step (a) of the method, an untreated feed stream and a guard bed material are supplied. The guard bed material comprises any one of the compositions of this invention. The untreated (i.e., impure) feed stream comprises one or more hydrocarbons and undesirable impurities. In one or more embodiments, the impurities comprise at least one compound having at least one of the following elements: nitrogen, halogens, oxygen, sulfur, arsenic, selenium, tellurium, phosphorus, and Group 1 through Group 12 metals.

In step (b) of the method, at least a portion of the feed stream is contacted with the guard bed material under treatment conditions. At least a portion of the impurities from the feed stream are removed. A treated feed stream is thereby produced which has a reduced amount of impurities.

In one or more embodiments, the guard bed material, the feed stream and the guard bed are supplied to a guard bed zone for contacting therein. The reaction zone may be in a separate reactor. Optionally, the reaction zone may be in the same reactor, such as for example, in the top bed of a multi-bed reactor used for aromatic alkylation or other hyrocarbon conversion process.

The treatment conditions for the method include or comprises a temperature of from about 30° C. (ambient) to about 300° C., from about 100° C. to 200° C., or from about 100° C. to 125° C. The treatment pressure is from about 101 kPa (ambient) to about 4601 kPa, from about 101 kPa to about 3000 kPa, and from about 101 kPa to about 2500 kPa. The treatment weight hourly space velocity (WHSV) is in the range from about 5 to 70 $hr^{-1}$, preferably 12 to 45 $hr^{-1}$, based on the weight of the at least partially untreated alkylatable aromatic compound. When operated as a non-reactive guard bed, the treatment conditions are preferably at ambient conditions. When operated as a reactive guard bed, the treatment conditions are substantially the same as the alkylation conditions, preferably, at least partially liquid phase conditions.

In operation of a method for removing impurities from a hydrocarbon stream, an untreated feed stream is supplied, preferably to a guard bed zone either in a separate vessel or a portion of another reactor. The untreated (i.e., impure) feed stream contains hydrocarbon and undesireable impurities, as defined herein. Preferably, the hydrocarbon comprises an alkylatable aromatic compound, such as benzene, and optionally an alkylating agent, such as ethylene or propylene. The reaction zone contains any one of the guard bed materials of the first aspect of the invention. The untreated feed stream is contacted with the guard bed material under treatment conditions to remove at least a portion of the impurirtes. A treated feed stream is produced thereby which has a reduced amount of impurities, preferably reduced by 10 wt. % or more as compared to the untreated feed stream. When the amount of the impurities are reduced, the cycle length of the downstream catalysts are increased due to less catalyst poisons being present.

Process for Producing Mono-Alkylated Aromatic Compounds

Still anotheer aspect of this invention is a process for producing a mono-alkylated aromatic compound. In an alkylation step (a) of the process, at least a portion of a treated feed stream and an alkylating agent stream is contacted with an alkylation catalyst under suitable at least partially liquid phase reaction conditions. The treated feed stream comprises an alkylatable aromatic compound, defined below, which is preferably benzene. It is made by the method for removing impurities from a hydrocarbon stream, such as the untreated feed stream, of the second aspect of this invention. The alkylating agent, defined below, is typically an olefin, preferably ethylene or propylene.

Preferably, the treated feed stream is supplied to an alkylation reaction zone where the contacting in alkylation step (a) preferably occurs. At least a portion of the alkylatable aromatic compound in the treated feed stream is alkylated with said alkylating agent stream to produce an effluent stream. The effluent stream comprises the mono-alkylated aromatic compound and poly-alkylated aromatic compounds. In separation step (b), the effluent stream is separated to recover a mono-alkylated aromatic compound stream and a poly-alkylated aromatic compounds stream.

The alkylation catalyst is the same or different from the guard bed material. The alkylation catalyst comprises an acidic aluminosilicate. The aluminosilicate is any one of a MCM-22 family molecular sieve, faujasite, mordenite, zeolite beta, or combinations of two or more thereof.

Additional mono-alkylated aromatic compound may be produced from the poly-alkylated aromatic compounds stream. Another portion of the treated feed stream is contacted with the poly-alkylated aromatic compound stream with a transalkylation catalyst under suitable at least partially liquid phase transalkylation conditions. The poly-alkylated aromatic compounds are transalkylated with the alkylatable aromatic compound, typically benzene, to produce additional said mono-alkylated aromatic compound.

The transalkylation catalyst is a large pore molecular sieve, preferably, having a Constraint Index of less than 2. Alternatively, the transalkylation catalyst is a MCM-22 family material, as defined herein.

In one or more embodiments, the alkylatable aromatic compound is benzene. In this instance, when the alkylating agent is ethylene, then the mono-alkylated aromatic compound is ethylbenzene and an example of one of the poly-alkylated aromatic compounds is poly-ethylbenzene. However, when the alkylating agent is propylene, then the mono-alkylated aromatic compound is cumene, and an example of one of the poly-alkylated aromatic compounds is poly-isopropylbenzene.

In one or more embodiments of the alkylation step (a), an alkylating agent is supplied to a guard bed zone along with the guard bed material and the untreated feed stream. In such guard bed zone, the alkylating agent stream is contacted with said guard bed material and said untreated feed stream to produce an additional effluent stream which comprises additional mono-alkylated and poly-alkylated aromatic compounds. At the same time the alkylation reaction occurs, the impurities are removed. In this embodiment, the guard bed zone may be referred to as a reactive guard bed (RGB).

In one or more embodiments of the alkylation step (c), the another portion of said untreated feed stream which may comprise undesirable impurites may be first contacted with any one of the guard bed materials of this invention. When contacted with such guard bed material, at least a portion of the impurities are removed to produce a treated feed stream.

When no alkylating agent is supplied to the guard bed zone, the zone is an adsoprtion zone and is called a non-reactive guard bed. After contact with the guard bed material, a treated feed stream having a reduced amount of impurities is produced; however, no alkylated aromatic compound, such as additional mono-alkylated and poly-alkylated aromatic compounds, is produced.

When alkylating agent is supplied to the guard bed zone, however, the zone is a reactive zone and is called a reactive guard bed. After contact with the guard bed material, a treated feed stream having a reduced amount of impurities is produced along with an additional amount of alkylated aromatic compound is produced.

The guard bed zone may be in a separate vessel or reactor, or it may be the first stage of the alkylation or transalkylation reaction zone. The guard bed zone is upstream from the alkylation reaction zone.

In operation of a process for producing a mono-alkylated aromatic compound, at least a portion of a treated feed stream which comprises an alkylatable aromatic compound, typically benzene, is contacted with an alkylating agent stream which comprises an alkylating agent, typically an olefin such as ethylene or propylene, in the presence of an alkylation catalyst under suitable at least partially liquid phase alkylation conditions. At least a portion of the alkylatable aromatic compound is alkylated with the alkylating agent in the alkylating agent stream to produce an effluent stream which comprises the mono-alkylated aromatic compound and poly-alkylated aromatic compounds. The effluent stream may be separated to recover the mono-alkylated aromatic compound stream, such as an ethylbenzene or cumene stream, and the poly-alkylated aromatic compound for further processing. The poly-alkylated aromatic compound stream may be contacted with another portion of the treated feed stream in the presence of a transalkylation catalyst under suitable at least partially liquid phase transalkylation conditions to produce an effluent stream comprising additional mono-alkylated aromatic compound.

Alkylatable Aromatic Compounds

Suitable alkylatable aromatic hydrocarbons for any one of the embodiments of this invention include benzene, naphthalene, anthracene, naphthacene, perylene, coronene, and phenanthrene, with benzene being preferred.

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds for any one of the embodiments of this invention include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing substantial quantities of benzene, toluene and/or xylene constitutes a useful feed for the process of this invention.

Alkylating Agents

The alkylating agents, which are useful in one or more embodiments of this invention, generally include any aliphatic or aromatic organic compound having one or more available alkylating olefinic groups capable of reaction with the alkylatable aromatic compound, preferably with the alkylating group possessing from 1 to 5 carbon atoms, or poly-alkylated aromatics compound(s). Examples of suitable alkylating agents for any one of the embodiments of this invention are olefins such as ethylene, propylene, the butenes, and the pentenes; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds suitable for one or more embodiments of this invention include, but are not limited to, polyethylbenzene(s), polyisporpoylebenzene(s) and mixtures thereof.

For example, a typical FCC light olefin stream possesses the following composition as shown in Table 1:

TABLE 1

|  | Wt. % | Mol. % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Alkylation and/or Transalkylation Conditions

In one or more embodiments, the alkylation and/or transalkylation processes of this invention are conducted such that the organic reactants, i.e., the alkylatable aromatic compound and the alkylating agent, are brought into contact with an alkylation or transalkylation catalyst or guard bed material in a suitable alkylation or transalkylation reaction zone. Similarly, in the method for removing impurities from a hydrocarbon stream of this invention is conducted such that the organic reactants, i.e., feed stream comprising one or more hydrocarbons and undesirable impurites, are brought into contact with the guard bed material in a suitable treatment zone. Such reaction or treatment zones may be, for example, a flow reactor containing a fixed bed of the alkylation and/or transalkylation catalysts and/or guard bed material, under effective and suitable alkylation and/or transalkylation conditions or treatment conditions.

Such alkylation conditions can include or comprises at least one of the following: a temperature of from about 10° C. and about 400° C., or from about 10° C. to about 200° C., or from about 150° C. to about 300° C., a pressure up to about 25000 kPa, or up to about 20000 kPa, or from about 100 kPa to about 7000 kPa, or from about 689 kPa to about 4601 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 hr$^{-1}$ and about 100 hr$^{-1}$, or from about 0.5 hr$^{-1}$ to 50 hr$^{-1}$, or from about 10 hr$^{-1}$ to about 100 hr$^{-1}$.

The reactants can be in either the vapor phase or in the liquid phase, or in the at least partially liquid phase. In one or more embodiments, the reactants can be neat, i.e., free from intentional admixture or dilution with other material, or they can include carrier gases or diluents such as, for example, hydrogen or nitrogen.

When benzene is alkylated with ethylene to produce ethylbenzene, the alkylation reaction may be carried out under at least partially liquid phase conditions including a temperature between about 150° C. and 300° C., or between about 200° C. and 260° C., a pressure up to about 20000 kPa, preferably from about 200 kPa to about 5600 kPa, a WHSV of from about 0.1 hr$^{-1}$ to about 50 hr$^{-1}$, or from about 1 hr$^{-1}$ and about 10 hr$^{-1}$ based on the ethylene feed, and a ratio of the benzene to the ethylene in the alkylation reactor from 1:1 molar to 30:1 molar, preferably from about 1:1 molar to 10:1 molar.

When benzene is alkylated with propylene to produce cumene, the reaction may be carried out under at least partially liquid phase conditions including a temperature of up to about 250° C., preferably from about 10° C. to about 200° C.; a pressure up to about 25000 kPa, preferably from about 100 kPa to about 3000 kPa; and a WHSV of from about 1 hr$^{-1}$ to about 250 hr$^{-1}$, preferably from 5 hr$^{-1}$ to 50 hr$^{-1}$, preferably from about 5 hr$^{-1}$ to about 10 hr$^{-1}$ based on the ethylene feed.

Such transalkylation conditions can include at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 hr$^{-1}$ to about 100 hr$^{-1}$ on total feed, and aromatic/poly-alkylated aromatic compound weight ratio 1:1 to 6:1.

When the poly-alkylated aromatic compounds are poly-ethylbenzenes and are reacted with benzene to produce ethylbenzene, the transalkylation conditions include or comprises a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are poly-isopropylbenzenes (PIPBs) and are reacted with benzene to produce cumene, the transalkylation conditions include or comprises a temperature of from about 100° C. to about 200° C., a pressure of from about 300 kPa to about 400 kPa, a weight hourly space velocity of 1 to 10 on total feed and benzene/PIPB weight ratio 1:1 to 6:1.

EXAMPLES

The invention will now be more particularly described with reference to the following Examples. Numerous modifications and variations are possible and it is to be understood that within the scope of the appended claims, the invention may be practiced otherwise than as specifically described herein.

Experimental
Alpha Value

The Alpha Value tests for the guard bed materials or compositions in the Examples were performed in accordance with the methods described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test included a constant temperature of 538° C. and a variable flow rate as described in detail in the Journal of Catalysis, Vol. 61, p. 395 (1980).

Collidine Uptake

The Collidine Uptake for the samples of the guard bed materials or compositions in the Examples was determined as the millimoles of collidine (a type of catalyst poison) absorbed per gram of guard bed material or composition sample that is dried under nitrogen flow at 200° C. for 60 minutes on a Thermogravametric Analyzer (Model Q5000, manufactured by TA Instruments, New Castle, Del.). After drying the sample, the collidine (as a catalyst poison) was sparged over the sample for 60 minutes at a collidine partial pressure of 3 torr. The Collidine Uptake was calculated from the following formula: (sample weight after sparging with collidine−dried sample weight)×106÷(molecular weight of collidine×dried sample weight). When the sample weight and the dried sample weight is measured in grams, the molecular weight of collidine is 121.2 grams per millimole.

Temperature Programmed Ammonia Desorption

Temperature programmed ammonia desorption (TPAD) for the samples of the guard bed material or composition in the Examples was determined according to techniques well known in the art. For the TPAD analysis of the samples, a sample (0.2 g) was first dried at 500° C. for 3 hours under a helium (He) flow rate of 10 cc/min. The temperature was then reduced to 100° C. whereupon the sample was saturated with ammonia gas. After saturation with ammonia gas, the sample was desorbed at 100° C. with helium flow to desorb physisorbed ammonia from the sample. TPAD was performed at a desorption temperature ramp of 18.4° C./min under helium flow rate of 16 cc/min. The desorbed ammonia and water (if any) were monitored during the TPAD and expressed as milliequivalents of H+ sites per gram of sample (meq/g).

Example 1

Synthesis of Zeolite Beta with Pseudoboehmite Alumina Composition

Eighty (80) parts zeolite beta zeolite crystals were combined with 20 parts of a source of pseudoboehmite alumina, on a calcined dry weight basis. The pseudoboehmite alumina sources were: VERSAL-300™, obtainable from Honeywell UOP; PURAL NG™, obtainable from Sasol North America Inc.; and CATAPAL-200™, obtainable from Honeywell UOP. The zeolite beta and the pseudoboehmite alumina dry powder were placed in a muller or a mixer and mixed for about 10 to 30 minutes. Sufficient water and nitric acid was added to the zeolite beta and alumina during the mixing process to produce an extrudable paste. The extrudable paste was formed into a ¹⁄₂₀ inch quadrulobe extrudate using an extruder. After extrusion, the ¹⁄₂₀ inch quadrulobe extrudate was dried at a temperature ranging from 250° F. (121° C.) to 325° F. (168° C.). The dried extrudate was then calcined in a nitrogen/air mixture to a temperature between 850° F. (454° C.) and 1069° F. (576° C.).

Example 2

Synthesis of Zeolite Beta with Titania Composition

Eighty (80) parts zeolite beta zeolite crystals were combined with 20 parts of a source of titania, on a calcined dry weight basis. The titania source was: AEROXIDE P-25™ titania, TiO$_2$, obtainable from Sigma-Aldrich. The zeolite beta and titania dry powder were placed in a muller or a mixer and mixed for about 10 to 30 minutes. Sufficient water and nitric acid was added to the zeolite beta and titania during the mixing process to produce an extrudable paste. The extrudable paste was formed into a 1/20 inch quadrulobe extrudate using an extruder. After extrusion, the 1/20 inch quadrulobe extrudate was dried at a temperature ranging from 250° F. (121° C.) to 325° F. (168° C.). The dried extrudate was then calcined in a nitrogen/air mixture to a temperature between 850° F. (454° C.) and 1069° F. (576° C.).

Example 3

Synthesis of Zeolite Beta with Amorphous Silica-Alumina Composition

Eighty (80) parts zeolite beta zeolite crystals were combined with 20 parts of a source of amorphous, precipitated silica-alumina, on a calcined dry weight basis. The sources of amorphous, precipitated silica-alumina were: SIRAL-20™ and SIRAL-40™, obtainable from Sasol North America, Inc. The zeolite beta and the silica-alumina dry powder were placed in a muller or a mixer and mixed for about 10 to 30 minutes. Sufficient water and nitric acid was added to the zeolite beta and the silica-alumina during the mixing process to produce an extrudable paste. The extrudable paste was formed into a 1/20 inch quadrulobe extrudate using an extruder. After extrusion, the 1/20 inch quadrulobe extrudate was dried at a temperature ranging from 250° F. (121° C.) to 325° F. (168° C.). The dried extrudate was then calcined in a nitrogen/air mixture to a temperature between 850° F. (454° C.) and 1069° F. (576° C.).

Example 4

Synthesis of Self-bound Alumina and Silica-Alumina Amorphous Materials

The source of the amorphous alumina was VERSAL-300™. The source of amorphous, precipitated silica-alumina powder was (SIRAL-20™). The amorphous alumina or precipitated silica-alumina powder were each placed in a muller or a mixer and mixed for about 10 to 30 minutes. Sufficient water and nitric acid was added to the amorphous alumina or precipitated silica-alumina during the mixing process to produce an extrudable paste. The extrudable paste was formed into a 1/20 inch quadrulobe extrudate using an extruder. After extrusion, the 1/20 inch quadrulobe extrudate was dried at a temperature ranging from 250° F. (121° C.) to 325° F. (168° C.). The dried extrudate was then calcined in a nitrogen/air mixture to a temperature between 850° F. (454° C.) and 1069° F. (576° C.).

Performance Evaluation

The extrudate composition and materials of Examples 1 to 4, described above, were characterized for activity and for poison capacity of the reactive guard bed during alkylation service by testing the acidity by the amount of acid sites on these materials as measured by TPAC and Collidine Uptake. These acid sites are known in the art for providing the poison capacity of these material while in service in an absorptive (non-reactive) or reactive guard bed.

One method to measure acidity is by the Alpha Value (a standard hexane cracking test). A second method to measure acidity is to determine the total Collidine Uptake on a mass basis in a material. A third method to measure acidity is TPAD which measures the amount of ammonia adsorbed on the material at a particular temperature and then determine the amount of ammonia desorbed from that material as the temperature is increased.

Example 5

Alpha Value Evaluation

The results of the Alpha Value test are included in the Table 2 below. The amorphous, precipitated silica-alumina SIRAL-20™ and SIRAL-40™ binders have higher Alpha Value when extruded with zeolite beta than the samples of self-bound alumina. The Alpha Value of the amorphous self-bound alumina, VERSAL-300™, and the self-bound precipitated silica-alumina, SIRAL-20™, was very low compared to all of the binders that have been combined with zeolite beta. Thus, the increase in Alpha Value, a measure of hexane cracking activity, was unexpected as the contribution of the SIRAL-20™ to the Alpha Value of the mixture of SIRAL-20™ and zeolite beta should be minor if the acidity was only from the physical addition of the SIRAL-20™ material. This unexpected result shows a significant advantage for the amorphous, precipitated silica-alumina bound formulations for RGB service. In addition, the pseudoboehmite aluminas tested, PURAL NG™ and CATAPAL-200™, had higher Alpha Value than VERSAL-300™. The AEROXIDE P-25™ titania material had a lower Alpha Value than the alumina and amorphous, precipitated silica-alumina materials.

TABLE 2

| Binder Type | Zeolite Beta Crystal:Binder Ratio | Oxide | Alpha |
|---|---|---|---|
| VERSAL-300 ™ | 80/20 | Al$_2$O$_3$ | 470 |
| PURAL NG ™ | 80/20 | Al$_2$O$_3$ | 600 |
| CATAPAL-200 ™ | 80/20 | Al$_2$O$_3$ | 550 |
| AEROXIDE P-25 ™ | 80/20 | TiO$_2$ | 340 |
| SIRAL-20 ™ | 80/20 | 20SiO$_2$—80Al$_2$O$_3$ | 750 |
| SIRAL-40 ™ | 80/20 | 40SiO$_2$—60Al$_2$O$_3$ | 760 |
| SIRAL-20 ™ | 0/100 | 20SiO$_2$—80Al$_2$O$_3$ | 31 |
| VERSAL-300 ™ | 0/100 | Al$_2$O$_3$ | 1.8 |

The physical properties of SIRAL-20™, PURAL NG™ and VERSAL-300™ are shown in Table 3 below. The cumulative particle size distribution d$_{50}$ may be determined on a Horiba Light scattering particl analyzer. SIRAL-20™ and PURAL NG™ have a larger particle size and lower pore volume than VERSAL-300™.

TABLE 3

| | VERSAL-300 ™ Al$_2$O$_3$ | PURAL NG ™ Al$_2$O$_3$ | SIRAL-20 ™ SiO$_2$—Al$_2$O$_3$ |
|---|---|---|---|
| Surface Area (m$^2$/g)* | 300 | 170 | 420 |
| Particle Size d$_{50}$ (μm) | 20 | 35 | 50 |
| Pore Volume (cc/g) | 1 | 0.45 | 0.75 |

*After activation at 550° C. for 3 hours.

Not to be bound by any theory, it is believed that the higher acidity of the PURAL NG™ alumina as compared to the VERSAL-300™ alumina may be due to the greater accessibility to the acid sites as the lower surface area and larger particle size of PURAL NG™ may help form a more open pore network. In addition to the unexpected formation of acid sites from the mixture of SIRAL-20™ and zeolite beta, the larger particle size for the SIRAL-20™ likely also helps make more acid sites accessible.

Example 6

Temp. Programmed Ammonia Desorption and Collidine Adsorption Evaluations

Figure 2:
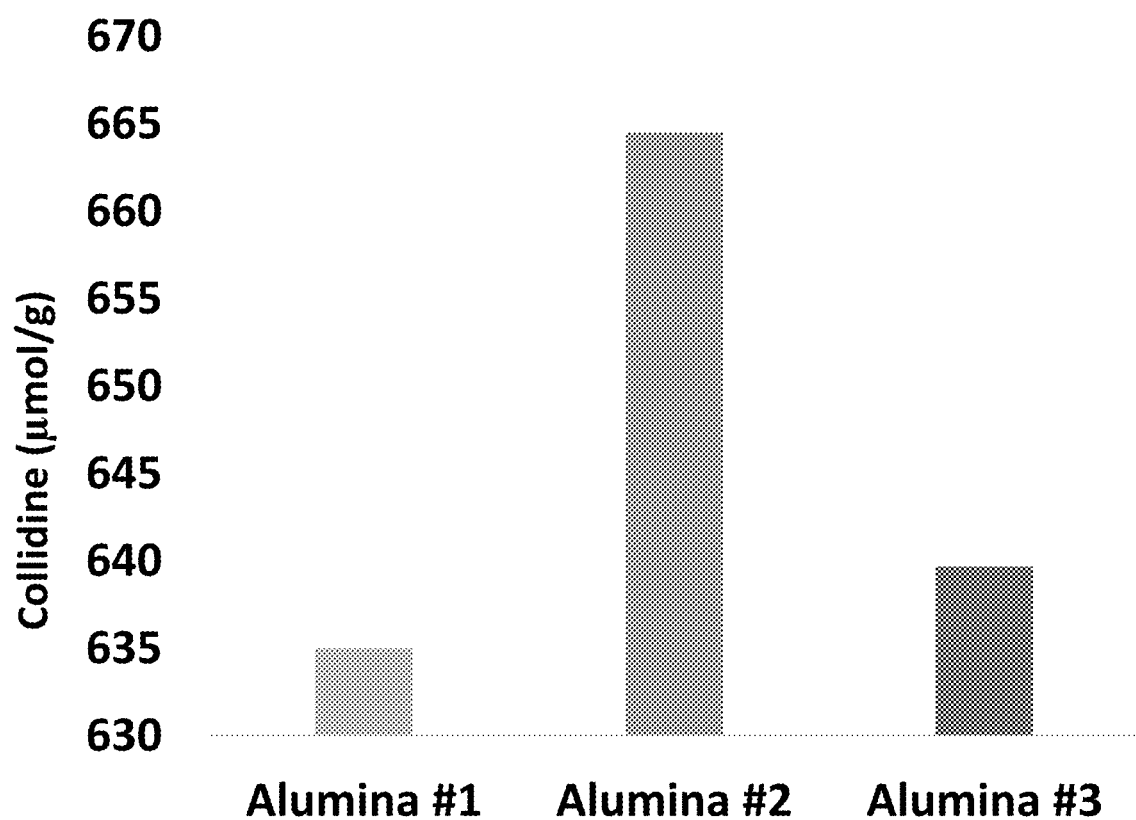
FIG. 2 shows the performance of the guard bed materials of Example 6 as measured by Collidine Uptake for the pseudoboehmite aluminas, VERSAL-300™ (Alumina #1) and PURAL NG™ (Alumina #2) and the amorphous, preciptated silica-alumina, SIRAL-20™ (Alumina #3).

The results of the temperature programmed ammonia desorption (TPAD) test are included in Table 4 below. FIG. 1 shows a comparison of Binder 1, VERSAL-300™, a pseudoboehmite alumina (having a $d_{50}$ particle size of 20 μm) to Binder 2, PURAL NG™, a pseudoboehmite alumina (having a $d_{50}$ particle size greater than 20 μm) and Binder 3, SIRAL-20™, an amorphous, precipiated silica-alumina. An increase in the TPAD was observed for both of the materials. A slightly lower TPAD was observed for the CATAPAL-200™ and SIRAL-40™ bound materials. Thus, the silica content in the silica-alumina binder would preferentially be lower than 40% to maximize the TPAD and collidine acid site count. The AEROXIDE P-25 titania material has lower TPAD than the alumina and silica-alumina materials. An almost identical trend was observed in the collidine adsorption capacity in Table 4 below and in FIG. 2.

constant in units of cc gmol$^{-1}$ hr$^{-1}$. The DIPB selectivity of the catalyst composition was determined by calculating the ratio of diisopropylbenzene to cumene production. Thus, a lower selectivity to DIPB represents a more monoselective alkylation catalyst. These catalytic activity and selectivity data were normalized based on the 80/20 Zeolite Beta/VERSAL-300™ Al$_2$O$_3$ data.

While the primary purpose of the reactive guard bed (RGB) was the adsorption or removal of poisons, a secondary responsibility was the aromatic alkylation of an olefin with benzene. The catalyst activity of the catalyst composition can be a key variable for determining when to replace the RGB catalyst composition as the adsorption of poisons will decrease the activity of the catalyst. This leading indicator can prevent breakthrough of poisons to the main alkylator bed. As can be seen in Table 5 below, the amorphous, precipitated silica-alumina SIRAL-20™ bound with zeolite beta catalyst composition has a higher activity for aromatic alkylation (as measured by the normalized rate constant, k) than the psuedobohemite alumina VERSAL-300™ bound with zeolite beta compositionin which both

TABLE 4

| Binder Type | Zeolite Beta Crystal: Binder Ratio | Oxide | TPAD (meq/g) | Collidine (μmol/g) |
|---|---|---|---|---|
| VERSAL-300 ™ | 80/20 | Al$_2$O$_3$ | 0.78 | 635 |
| PURAL NG ™ | 80/20 | Al$_2$O$_3$ | 0.83 | 665 |
| CATAPAL-200 ™ | 80/20 | Al$_2$O$_3$ | 0.72 | 601 |
| AEROXIDE P-25 ™ | 80/20 | TiO$_2$ | 0.55 | 500 |
| SIRAL-20 ™ | 80/20 | 20SiO$_2$—80Al$_2$O$_3$ | 0.82 | 640 |
| SIRAL-40 ™ | 80/20 | 40SiO$_2$—60Al$_2$O$_3$ | 0.75 | 617 |
| SIRAL-20 ™ | 0/100 | 20SiO$_2$—80Al$_2$O$_3$ | 0.49 | 97 |
| VERSAL-300 ™ | 0/100 | Al$_2$O$_3$ | 0.41 | 8 |

Example 7

Cumene Activity Profile

The catalytic activity and selectivity for aromatic alkylation of each catalyst composition was determined by testing the material for cumene alkylation. The cumene alkylation test consists of loading the dried catalyst into a batch reactor along with benzene. The reactor was then composition have identical DIPB/IPB selectivity. The self-bound SIRAL-20™ composition has a significantly lower activity than the zeolite containing composition, but does have a higher activity than the inert self-bound VERSAL-300™ alumina, where the activity is measured by the normalized rate constant, k. The low selectivity to the DIPB for the self-bound SIRAL-20™ composition is likely the result of low conversion on a low catalytic activity composition.

TABLE 5

| Binder Type | Zeolite Beta Crystal:Binder Weight Ratio | Oxide | Normalized Rate Constant, k | Normalized DIPB/IPB Selectivity |
|---|---|---|---|---|
| VERSAL-300 ™ | 80/20 | Al$_2$O$_3$ | 1 | 1 |
| SIRAL-20 ™ | 80/20 | 20SiO$_2$—80Al$_2$O$_3$ | 1.3 | 1 |
| SIRAL-20 ™ | 0/100 | 20SiO$_2$—80Al$_2$O$_3$ | 0.19 | 0.54 |
| VERSAL-300 ™ | 0/100 | Al$_2$O$_3$ | 0 | 0 | heated to 266° F. followed by the addition of propylene under an inert gas pressure of 300 psig. Samples of the catalyst composition were removed periodically for the duration of the test and analyzed with gas chromatography to determine the catalytic activity and selectivity of benzene alkylation with propylene. The catalytic activity of the catalyst composition was evaluated by monitoring the conversion of benzene and propylene as a function of time and determining a rate constant, k, which was 10$^3$ times the rate Also, the normalized DIPB/IPB selectivity data also differentiates the alternative SIRAL-20™ amorphous, precipitated silica-alumina binder from the prior art. This binder itself is active for benzene alkylation in addition to providing a higher poison capacity. That is, the amorphous, precipitated silica-alumina binder does not decrease the monoselectivity (by making more DIPB or heavier) but also increases the capacity to absorb catalyst poisons.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A method for removing impurities from a hydrocarbon stream, the method comprising the steps of:
   (a) supplying a portion of an untreated feed stream, said feed stream comprising one or more hydrocarbons and undesirable impurities, said impurities comprise at least one compound having at least one of the following elements: nitrogen, halogens, oxygen, sulfur, arsenic, selenium; tellurium, phosphorus, and Group 1 through Group 12 metals,
   (b) supplying a guard bed material which comprises a zeolite having a Constraint Index of less than 3 and a mesoporous binder,
   wherein said mesoporous binder comprises amorphous silica-alumina and has a particle diameter of greater than or equal to 20 µm at 50% of the cumulative particle size distribution ($d_{50}$), a pore volume of less than 1 cc/g and an alumina content greater than or equal to 75%, by weight,
   wherein the ratio of said zeolite to said mesoporous metal oxide is in the range from 95:5 to 5:95, by weight,
   wherein said guard bed material has one or more of the following properties:
      (i) an Alpha Value of greater than or equal to 500,
      (ii) a Collidine Uptake of greater than or equal to 600 µmoles/g, and
      (iii) a Temperature Programmed Ammonia Desportion of greater than or equal to 0.70 meq/g; and
   (c) contacting said portion of said untreated feed stream with said guard bed material under treatment conditions to remove at least a portion of said impurities and produce a treated feed stream having a reduced amount of impurities.

2. The method of claim 1, wherein said zeolite has a framework structure which includes one or more of BEA*, FAU, MOR, and MWW.

3. The method of claim 2, wherein said framework structure of BEA* comprises zeolite beta, said framework structure of FAU includes one or more of faujasite, zeolite Y, USY, Deal-Y, UHP-Y, and REY, said framework structure of MOR includes one or more of mordenite, TEA-mordenite, EMM-34, and UZM-14, or said framework structure of MWW comprises a MCM-22 family material selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, MIT-1, ITQ-1, ITQ-2, ITQ-30, and mixtures of two or more thereof.

4. A process for producing a mono-alkylated aromatic compound, the process comprising the step of:
   (a) supplying a portion of an untreated feed stream, said feed stream comprising one or more alkylatable aromatic compounds and undesirable impurities, said impurities comprise at least one compound having at least one of the following elements: nitrogen, halogens, oxygen, sulfur, arsenic, selenium, tellurium, phosphorus, and Group 1 through Group 12 metals;
   (b) supplying a guard bed material which comprises a zeolite having a Constraint Index of less than 3 and a mesoporous binder,
   wherein said mesoporous binder comprises amorphous silica-alumina, and has a particle diameter of greater than or equal to 2 µm at 50% of the cumulative particle size distribution ($d_{50}$), a pore volume of less than 1 cc/g and an alumina content greater than or equal to 75%, by weight,
   wherein the ratio of said zeolite to said mesoporous metal oxide is in the range from 95:5 to 5:95, by weight,
   wherein said guard bed material has one or more of the following properties:
      an Alpha Value of greater than or equal to 500,
      (ii) a Collidine Uptake of greater than or equal to 600 µmoles/g, and
      (iii) a Temperature Programmed Ammonia Desportion of greater than or equal to 0.70 meq/g;
   (c) contacting said portion of said untreated feed stream with said guard bed material under treatment conditions to remove at least a portion of said impurities and produce a treated feed stream having a reduced amount of impurities and said alkylatable aromatic compounds; and
   (d) contacting at least a portion of said treated feed stream and an alkylating agent stream in the presence of an alkylation catalyst under suitable at least partially liquid phase alkylation conditions to alkylate at least a portion of said alkylatable aromatic compounds with said alkylating agent stream to produce an effluent stream comprising said mono-alkylated aromatic compound and poly-alkylated aromatic compounds.

5. The process of claim 4; wherein a second stream of said alkylating agent is provided to contact said guard bed material and said feed stream in step (c) to produce additional mono-alkylated and poly-alkylated aromatic compounds while said impurities are removed.

6. The process of claim 4, wherein said alkylation catalyst comprises an acidic aluminosilicate.

7. The process of claim 6, wherein said aluminosilicate is any one of a MCM-22 family molecular sieve, faujasite, mordenite, zeolite beta, or combinations of two or more thereof.

8. The process of claim 7, wherein said MCM-22 family molecular sieve is any one of MCM-22, PSH-3, SSZ-25, MCM-36, MCM-49, MCM-56, ERB-1, EMM-10, EMM-10-P, EMM12, EMM-13, UZM-8, UZM-8HS, UZM-37, ITQ-1, ITQ-2, ITQ-30, NET-1, or combinations of two or more thereof.

9. The process of claim 4, further comprising the steps:
(e) separating said effluent stream of step (d) to recover a mono-alkylated aromatic compound stream and a poly-alkylated aromatic compounds stream.

10. The process of claim 9, further comprising the step of:
(f) contacting said poly-alkylated aromatic compound stream and another portion of said treated feed stream in the presence of a transalkylation catalyst under suitable at least partially liquid phase transalkylation conditions to transalkylate said poly-alkylated aromatic compound stream with said alkylatable aromatic compound and produce additional said mono-alkylated aromatic compound.

11. The process of claim 10, wherein said transalkylation catalyst is a large pore molecular sieve or a MCM-22 family molecular sieve.

12. The process of claim 11, wherein said large pore molecular sieve is selected from the group of consisting of zeolite beta, faujasite, zeolite Y, Ultrastable Y (USY), Dealuminized Y (Deal Y), Rare Earth Y(REY), Ultrahydrophobic Y (UHP-Y), mordenite, TEA-mordenite, EMM-34, ZSM-2, ZSM-3, ZSM-4, ZSM-12, ZSM-14, ZSM-18, ZSM-20, ZSM-50, MCM-68, ECR-4, ECR-17, ECR-32, ECR-35 and mixtures of two or more thereof.

13. The process of claim 11, wherein said MCM-22 family molecular sieve is any one of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, ITQ-1, TrQ-2, ITQ-30, MIT-1, or combinations of two or more thereof.

14. The process of claim 4, wherein said alkylatable aromatic compound is benzene, said alkylating agent is ethylene, said mono-alkylated aromatic compound is ethylbenzene and said poly-alkylated aromatic compound is poly-ethylbenzene.

15. The process of claim 4, wherein said alkylatable aromatic compound is benzene, said alkylating agent is propylene, said mono-alkylated aromatic compound is cumene and said poly-alkylated aromatic compound is poly-isopropylbenzene.

* * * * *